United States Patent [19]

Langhals

[11] Patent Number: 4,677,076
[45] Date of Patent: Jun. 30, 1987

[54] PROCESS FOR DETERMINING WATER IN SAMPLES CONTAINING WATER

[76] Inventor: Heinz Langhals, Sundgauallee 55, D-7800 Freiburg, Fed. Rep. of Germany

[21] Appl. No.: 496,525

[22] Filed: May 24, 1983

Related U.S. Application Data

[63] Continuation of Ser. No. 322,571, Nov. 18, 1981, abandoned.

[30] Foreign Application Priority Data

Nov. 21, 1980 [DE] Fed. Rep. of Germany ....... 3043897

[51] Int. Cl.$^4$ ........................................... G01N 33/18
[52] U.S. Cl. ..................................... 436/40; 436/164
[58] Field of Search ................ 250/373, 252; 356/409, 356/414; 436/39, 40, 164, 172

[56] References Cited

U.S. PATENT DOCUMENTS 3,742,429  7/1973  Kawai ................................. 356/409
3,874,794  4/1975  Schmitt et al. .
4,267,572  5/1981  Witte ................................. 356/325 X

OTHER PUBLICATIONS

Hirt et al., Analytical Chemistry, vol. 26, No. 8, Aug. 1954, pp. 1270–1273.
ASTM, Manual On Recommended Practices in Spectrometry, 2nd Edition, 1966, General Techniques of Ultraviolet Quantitative Analysis, ASTM Designations E 169–163, pp. 65–71.
C. Reichardt and K. Dimroth, "Losungsmittel und empirische Parameter zur Charakterisierung ihrer Polaritat", Fortschritte der chemischen Forschung, vol. 11/1, pp. 1–73 (1968).
E. Kosower, "The Effect of Solvent on Spectra I., A New Empirical Measure of Solvent Polarity: Z–Values, II., Correlation of Spectral Absorption Data with Z–Values", Journal of the American Chemical Society, vol. 80, pp. 3253–3270 (1958).
C. Reichardt, Solvent Effects in Organic Chemistry (Monographs in Modern Chemistry, vol. 3), pp. 189–195 (Weinham, New York: Verlag Chemie, 1979).
M. Klessinger, "Konstitution und Lichtabsorption organischer Farbstoffe", Chemie in unserer Zeit, vol. 12, pp. 1–11 (1978).
Z. Maksimovic, C. Reichardt and A. Spiric, "Determination of Empirical Parameters of Solvent Polarity $E_T$ in Binary Mixtures by Solvatochromic Pyridinium–N–Phenol Betaine Dyes", Z. Anal. Chem., vol. 270, pp. 100–104 (1974).
C. Reichardt and R. Muller, "Der Substituenteneinfluss auf das Elektronenanregungsspektrum der Pyridinium-N-Phenolat-betaine", Justus Liebigs Annalen der Chemie, No. 11, pp. 1937–1963 (1976).
A. Vogel, A Textbook of Quantitative Inorganic Analysis, 4th Edition, pp. 687–690 (London: Longman, 1978).
K. Dimroth and C. Reichardt, "Die colorimetrische Analyse binarer organischer Losungsmittelgemische mit Hilfe der Solvatochromie von Pyridinium-N-phenolbetainen", Z. Analyt. Chem., vol. 215, pp. 344–350.
C. Reichardt, "Empirische Parameter der Losungsmittelpolaritat als lineare 'Freie Enthalpie'-Beziehungen", Angewandte Chemie, vol. 91, pp. 119–131 (1979).

Primary Examiner—Arnold Turk
Attorney, Agent, or Firm—Robbins & Laramie

[57] ABSTRACT

The invention relates to a process for determining water in samples containing water. This process is characterized in that a solvatochromic compound is added to a solution or dispersion of the sample in a solvent or directly to the liquid sample, the solvatochromism band $\lambda_{max}$ in the UV-vis-spectrum is determined, the $E_T$-value (molar excitation energy) of the solvatochromic compound is calculated and the water concentration is determined in accordance with the following equation:

$$c_{H_2O} = C^* \exp(E_T/E_D - E_T^0/E_D) - c^* \qquad (1)$$

in which
$E_T$ is the molar excitation energy of the solvatochromic compound,
$E_T^0$ is the $E_T$-value of the pure anhydrous solvent,
$c^*$ and $E_D$ are empirical parameters which may be taken from Tables or empirically determined.

14 Claims, 2 Drawing Figures

PROCESS FOR DETERMINING WATER IN SAMPLES CONTAINING WATER

This application is a continuation of application Ser. No. 322,571, filed Nov. 18, 1981, now abandoned.

BACKGROUND OF THE INVENTION

This invention relates to a process for determining water in water-containing, solid, liquid or gaseous samples, preferably in organic solvents. By means of the process according to the invention, it is readily possible to detect even traces of water.

PRIOR ART

At the present time, water is normally deteremined by Karl Fischer titration (A. I. Vogel "A Textbook of Quantitative Inorganic analysis", 4th Edition, Longman, London, 1978, page 688) which, apart from its sensitivity to interference, is difficult to carry out.

K. Dimroth and C. Reichardt [Z. Analyt. Chem. 215, 344 (1966)] report on studies of binary solvent mixtures using solvatachromic dyes. These authors observed that the position of the longest-wave band in the UV-spectrum of solvatochromic substances is greatly influenced by the solvent used. This property has proved to be particularly useful for characterising the polarity of solvents. In apolar solvents, such as dioxane for example, pyridinium-N-phenol betaines for example absorb in the long-wave region, whilst in polar solvents, such as methanol for example, they absorb in the short-wave region. The maximum of this solvatochromic absorption is termed $\lambda_{max}$. the molar excitation energy $E_T$ may be claculated from the absorption wavelength $\lambda_{max}$ in accordance with the following equation:

$$E_T = 28,950 \text{ (kcal.nm.mol}^{-1})/\lambda_{max}.$$

The authors drew up calibration curves for nine mixtures of organic solvents with water. These calibration curves enable the water content of a mixture of unknown composition to be determined. However, this known process is attended by the disadvantage that calibration curves first have to be drawn up and that it is time-consuming and laborious.

The $E_T$-values used in the above process are generally suitable for characterising the polarity of organic solvents and the $E_T$-scale is now the most frequently used polarity scale [cf. K. Dimroth and C. Reichardt "Angewandte Chemie" 91, 119 (1979); K. Dimroth and C. Reichardt "Fortschritte der chemischen Forschung", Vol. II/1, page 1 (1968)]

OBJECT OF THE INVENTION

The object of the present invention is to provide a simple and accurate rapid test for determining water, more particularly for determining water in organic solvents.

SUMMARY OF THE INVENTION

The present invention relates to a process for determining water in samples containing water which is characterised in that a solvatochromic compound is added to a solution or disperson of the sample in a solvent or directly to the liquid sample, the solvatochromism band $\lambda_{max}$ is determined in the UV-vis-spectrum, the $E_T$-value (molar excitation energy) of the solvatochromic substance is calculated and the water concentration is determined in accordance with the following equation.

$$c_{H_2O} = c^* \exp(E_T/E_D - E^\circ{}_T/E_D) - c^* \text{ tm (1)}$$

in which
$E_T$ represents the molar excitation energy of the solvatochromic compound;
$E^\circ{}_T$ represents the $E_T$-value of the pure, anhydrous solvent;
$c^*$ and $E_D$ are empirical parameters which may be taken from Tables or empirically determined.

BRIEF DESCRIPTION OF THE FIGS.

FIG. 1 contains a plot of $E_T 30$ against in $c_{H_2O}$ for a water-acetonitrile mixture.

FIG. 2 contains a plot of $E_T 30$ against $\ln(c_{H_2O}/c^* 1)$ for a water-acetonitrile mixture.

DETAILED DESCRIPTION OF THE INVENTION

Figure 1:
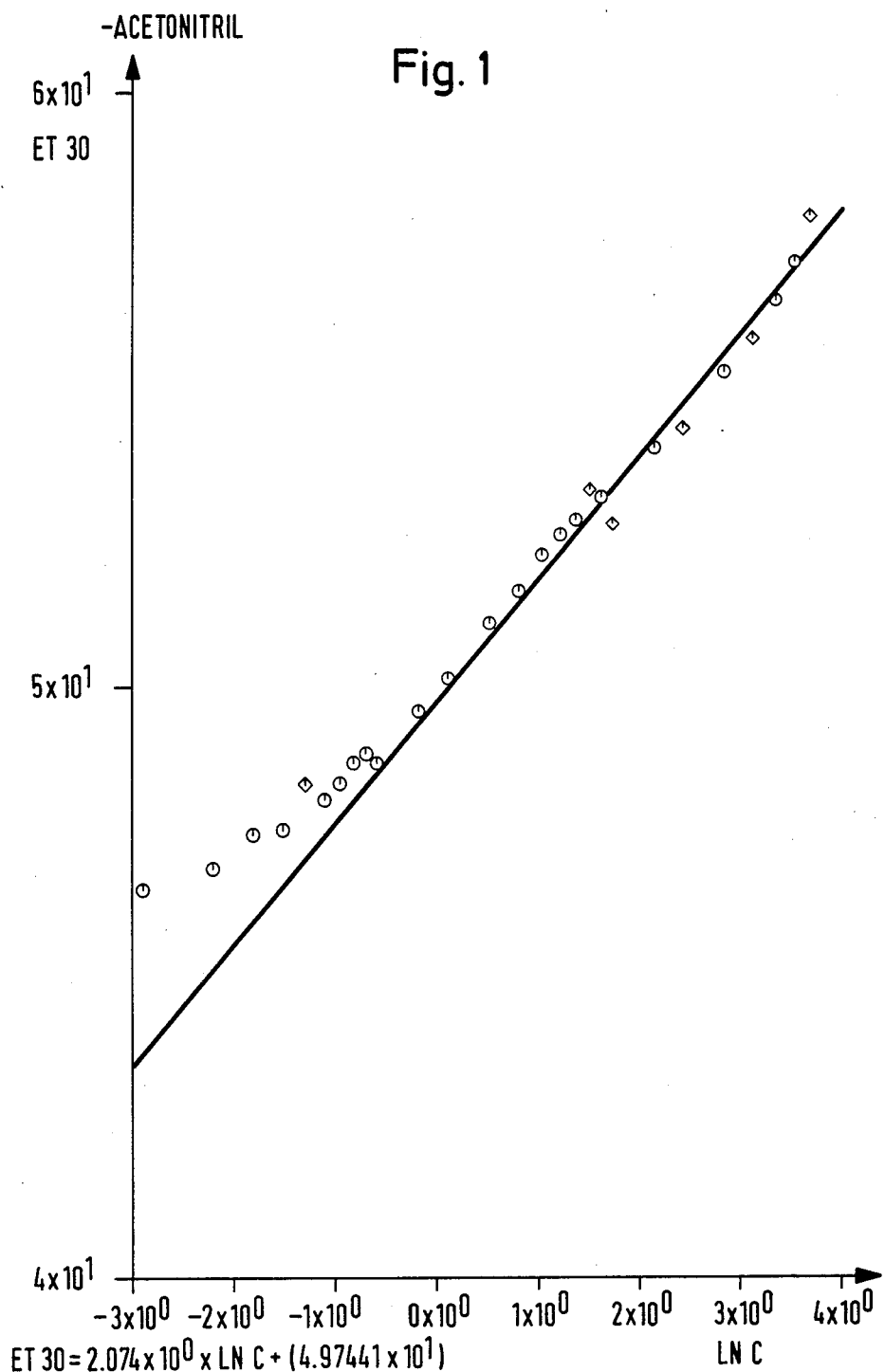

The Applicant has surprisingly found that, for all the aqueous systems studied, there is a connection between the $E_T$-values of solvatochromic substances and $c_{H_2O}$ according to equation (1) above.

The $E_T$-values may be calculated from $\lambda_{max}$ of the solvatochromism band of the solvatochromic substances in accordance with the following equation $$E_T = 28,590 \text{ kcal·nm}(kcal \cdot nm \cdot mol^{-1})/\lambda_{max} \quad (2)$$

To determine the $E_T$-values, the solvatochromic substance is dissolved in the solvent and $\lambda_{max}$ is measured in known manner. The concentrations are preferably selected in such a way that the extinction values at $\lambda_{max}$ lie in the extinction range from 0.4 to 1.2, preferably in the extinction range from 0.5 to 1.0 and, more preferably, in the extinction range from 0.7 to 1.0. Any suitable UV-spectrometer may be used for determining the $\lambda_{max}$-values $E_T(30)$ is the $E_T$ value using pyridinium phenol betaine.

Equation (1) is a two-parameter equation in which $c^*$ and $E_D$ may be determined for any solvent by a simple procedure in which solutions of water in the anhydrous solvents used for analysis of unknown concentration are prepared, a solvatochromic compound is added to the solutions and the $E_T$-values of these solutions are determined. The respective water contents of the solutions are then converted into concentrations and the $E_T$-values are plotted against ln $c_{H_2O}$ in a graph. The slope $E_D$ and the ordinate section b of the linear part are determined and $c^*$ is calculated in accordance with the following equation.

$$c^* = \exp[(E_T{}^\circ - b)/E_D] \quad (3)$$

The water concentrations may be converted into % by weight in accordance with the following equation:
% by weight $H_2O = C_{H_2O}$ [mol/1]·$MW_{H_2O}/(P$ solution [g/ml]·10) (4)

in which $c_{H_2O}$ represents the molar concentration of water, $Mw_{H_2O}$ represents the molecular weight of water and $\rho$ solution represents the density of the solution.

For frequency used solvents, the $c^*$ values are shown in Table I below. $E_T{}^\circ$ is the $E_T$-value of the pure anhydrous solvent. Determination of the values of Table I:

The $c_{H_2O}$-value is determined by a simple procedure. The pyridinium phenol betaine corresponding to the following formula

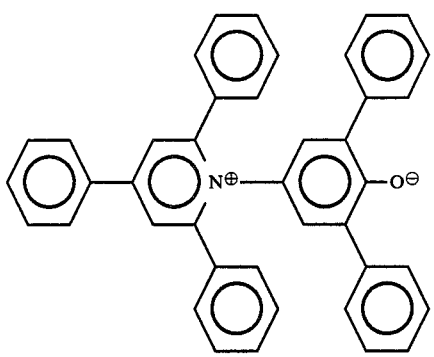

(I)

is dissolved in a small quantity (<5 mg) in the solvents to be studied. $\lambda_{max}$ of (I) in this solution is determined and the $E_T$-value is calculated by means of equation (2). This value is introduced into equation (1) with the $E_D$, $E_T°$ and $c^*$-values from Table (I) and $c_{H_2O}$ is calculated.

TABLE I

Constants of equation (1) for frequently used solvents

| Solvent | $E_T^{o(a,b)}$ | $c^{*(c)}$ | $E_D^{(a)}$ | $E_T°/E_D$ |
|---|---|---|---|---|
| Acetone | 42.4 | 0.31 | 2.83 | 14.9 |
| Acetonitrile | 46.0 | 0.15 | 2.07 | 22.2 |
| t-butyl alcohol | 43.9 | 1.01 | 2.82 | 15.6 |
| t-butyl hydroperoxide | 49.7 | 0.31 | 1.40 | 35.5 |
| dimethyl formamide | 43.8 | 11.43 | 9.24 | 4.74 |
| 1,4-dioxane$^{(d)}$ | 36.0 | 0.58 | 4.34 | 8.29 |
| Pyridine | 40.2 | 5.48 | 7.09 | 5.67 |

$^{(a)}$in kcal.mol$^{-1}$
$^{(b)}$see also C. Reichardt, Angew. Chem. 91, 119 (1979)
$^{(c)}$in mol.l$^{-1}$
$^{(d)}$in the case of fairly old samples rich in peroxide, it is advisable to add a base, for example piperidine.

Using the process according to the invention, it is possible to determine the water content of numerous of samples to be analysed. For example, the water content of liquid, gaseous and solid samples may be determined by the process according to the invention. In the case of liquid samples, the water content is directly determined in accordance with equation (1) using a solvatochromic dye. Examples of liquid samples are solvents (as a medium for chemical reactions, for paints and lacquers, as extractants). Gaseous samples are for example synthesis gases, smoke gases, etc. The process according to the invention may be used for example for determining the water content of gases after washing or scrubbing or for determining the dew point. It is also possible to analyse solid samples, for example to determine the water content of polymers, naturally occurring substances such as, for example, starch, cellulose, hydrate-forming substances, such as for example salts, samples of indefinite composition, such as for example soil samples or animal and vegetable tissue.

According to the invention, it is also possible to determine water in inorganic liquids, for example in mixtures of organic solvents with carbon disulphide. Suitable inorganic liquids are for example hydrazine hydrate, hydroxylamine, sulfur dioxide, hydrogen sulfide and ammonia (optionally at relatively low temperatures).

The solvents or dispersants used in the process according to the invention are, for example, acetone, acetonitrile, t-butyl alcohol, t-butyl hydroperoxide, dimethyl formamide, 1,4-dioxane or pyridine. Mixtures of these solvents may also be used. Other solvents which may be used are, for example, the solvents described in Angew. Chemie 91, pages 124 and 125 (1979).

In the process according to the invention, the water-containing samples may be used per se where they are solid or liquid. In general, however, solid or liquid samples will be dissolved or dispersed in one of the above-mentioned solvents. Emulsions or suspensions may also be used in the process according to the invention. There are no limitations regarding the type of solvent used as long as the solvent does not enter into any undesirable secondary reactions with the solvatochromic dye and the sample to be analysed. Where dispersions or suspensions are analysed by the process according to the invention, it is important to ensure that some of the light transmitted through is scattered. Although this phenomenon does not affect the position of $\lambda_{max}$, it can complicate the measurement. In such a case, a sensitive spectrometer may have to be used for determining $\lambda_{max}$.

It is not absolutely essential to use anhydrous solvents. It is also possible to use solvents having a low water content, in which case the determination of water is carried out by a differential method.

According to the invention, the solvatochromic substance used is the above-mentioned pyridinium phenol betaine of formula (I) or the so-called Kosower's dye corresponding to the following formula

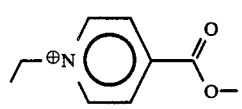

(II)

[E. M. Kasower, J. Am. Chem. Soc. 80, 3253 (1953)] or any one of the solvatochromic substances described by C. Reichardt in "Solvent Effects in Organic Chemistry" Verlag Chemie Weinheim, 1st Edition 1979, pages 193 and 194. It is particularly preferred to use the pyridinium phenol betaine of formula (I).

The process according to the invention may be carried out at room temperature. For determining the Table value and where highly accurate analytical results are required, the process according to the invention is preferably carried out at a constant temperature. However, this is not absolutely essential because the effect of temperature on the process according to the invention remains within very narrow limits.

The process may be carried out at any temperatures at which the dye used is heat-stable. At very high temperatures (>100° C.), the process becomes complicated because water evaportates from the solution whereas at temperatures below 0° C. water is able to crystallise out. Accordingly, temperatures in the range from 0° to 100° C. are preferred and temperatures around room temperature particularly preferred.

In one particularly preferred simplified embodiment of the invention, determination of the water content in accordance with equation (1) is carried out by visual colour comparison with a colour scale. To this end, the absorption colour of the solution or dispersion is visually compared with a colour scale (absorption colour as a function of $\lambda_{max}$ of the absorption) and $\lambda_{max}$ of the absorption is determined via this comparison.

The process according to the invention may also be carried out by absorbing the solvatochromic dyes to solids, for example to paper, so that test strips are obtained. These test strips are dipped into the solution to be studied. The test strip changes colour according to the water content and and the solvent used. $\lambda_{max}$ is determined by comparing the colour of the solution with an absorption colour $-\lambda_{max}$ colour scale (for example M. Klessinger, Chemie in unserer Zeit 12, 1 (1978) and $c_{H2O}$ is calculated on the basis of equation (1).

It is of particular importance to the result that there is a logarithmic relationship between the $E_T$-values and $c_{H2O}$ according to equation (1). Accordingly, the relative accuracy of the determination of $c_{H2O}$ is constant over a wide concentration range. $c_{H2O}$ may even be very accurately determined where the water concentrations are fairly low.

The invention is illustrated by the following Examples.

In all the following Examples, the UV-spectra are recorded with a Zeiss DMR 21 UV-spectrophotometer. Visual comparison of the solution with a colour scale is sufficient for approximate concentration determination.

EXAMPLE 1

General procedure for determining water in organic solvents:

A glass cuvette provided with a stopper (wall thickness 1 cm) is filled with the solution to be studied in the absence of moisture and with repeated rinsing of the cuvette with solvent. A small quantity (>5 mg) of the phenol betaine corresponding to formula (I) is added to the solvent and the position of the solvatochromism band $\lambda_{max}$ is determined in the UV-spectrum. The concentrations should be selected in such a way that $\lambda_{max}$ lies in the extinction range from 0.7 ... 1.0. For accurately locating max, the point at which the line connecting the radii intersects the absorption curve may be determined in accordance with the Mathias rule.

$\lambda_{max}$ is converted in accordance with equation (2) into the $E_T$-value which is subsequently introduced into equation (1) with the values $E_T°$, $c^*$ and $E_D$ of Table I and $c_{H2O}$ calculated.

EXAMPLE 2

General procedure for determining the parameters $E_D$ and $c^*$ of other solvents:

0.1, 1, 2 ... 9 ml of water are pipetted into a 10 ml measuring flask which is then made up to 10 ml with the anhydrous solvent to be analysed. As in the preceding Example, the $E_T$-values of these solutions are determined at 25° C. after addition of the pyridinium phenol betaine of formula (I). The respective water contents of the solutions are converted into concentrations.

In a graph, $E_T$ is plotted against ln $c_{H2O}$ and the slope $E_D$ and the ordinate section b of the linear part and determined. $c^*$ is calculated in accordance with equation (3), as stated in the specification.

The computer program POLAR is available for this procedure; this program also takes into account the measured values in the non-linear part of the graph.

EXAMPLE 3

Special procedure for determining the parameters $E_D$ and $c^*$ of the "water-acetonitrile" system:

Following the procedure of Example 2, the millilitres of water indicated in the following Table are pipetted into a 10 ml measuring flask which is then made up to 10 ml with acetonitrile.

Approximately 3 to 5 mg of the phenol betaine of formula (I) are added to the solvent and the position of the solvatochromism band $\lambda_{max}$ in the UV-spectrum is determined.

The $\lambda_{max}$-values are converted into the $E_T30$-values in accordance with equation (2).

The results obtained are shown in the following Table.

TABLE II

| ml H$_2$O[1] | $\lambda_{max}$ of the solvatochromism band of $E_T$ 30 in the respective solutions | ml H$_2$O converted into the molar concentration[2] | $\lambda_{max}$ converted into $E_T$ 30 | ln $c_{H2O}$ |
|---|---|---|---|---|
| 0.01 | 614.0 | 0.055 | 46.6 | −2.89 |
| 0.02 | 609.5 | 0.111 | 46.9 | −2.20 |
| 0.03 | 602.0 | 0.166 | 47.5 | −1.80 |
| 0.04 | 601.0 | 0.221 | 47.6 | −1.51 |
| 0.05 | 591.5 | 0.277 | 48.3 | −1.28 |
| 0.06 | 594.5 | 0.332 | 48.1 | −1.10 |
| 0.07 | 591.2 | 0.388 | 48.4 | −0.95 |
| 0.08 | 587.0 | 0.443 | 48.7 | −0.81 |
| 0.09 | 585.0 | 0.498 | 48.9 | −0.70 |
| 0.10 | 587.0 | 0.554 | 48.7 | −0.59 |
| 0.15 | 576.5 | 0.830 | 49.6 | −0.19 |
| 0.20 | 570.0 | 1.107 | 50.2 | 0.10 |
| 0.30 | 559.8 | 1.661 | 51.1 | 0.51 |
| 0.40 | 554.0 | 2.214 | 51.6 | 0.79 |
| 0.50 | 547.5 | 2.768 | 52.2 | 1.02 |
| 0.60 | 544.0 | 3.322 | 52.6 | 1.20 |
| 0.70 | 541.4 | 3.875 | 52.8 | 1.35 |
| 0.80 | 536.2 | 4.429 | 53.3 | 1.49 |
| 0.90 | 537.5 | 4.982 | 53.2 | 1.61 |
| 1.00 | 542.0 | 5.536 | 52.7 | 1.71 |
| 1.50 | 529.2 | 8.304 | 54.0 | 2.12 |
| 2.00 | 526.0 | 11.072 | 54.4 | 2.40 |
| 3.00 | 517.0 | 16.608 | 55.3 | 2.81 |
| 4.00 | 511.8 | 22.144 | 55.9 | 3.10 |
| 5.00 | 505.8 | 27.680 | 56.5 | 3.32 |
| 6.00 | 500.2 | 33.216 | 57.2 | 3.50 |

TABLE II-continued

| ml $H_2O$[1] | $\lambda_{max}$ of the solvatochromism band of $E_T$ 30 in the respective solutions | ml $H_2O$ converted into the molar concentration[2] | $\lambda_{max}$ converted into $E_T$ 30 | ln $c_{H_2O}$ |
|---|---|---|---|---|
| 7.00 | 493.5 | 38.752 | 57.9 | 3.66 |

[1]Made up to 10 ml with acetonitrile in each case
[2]The factor 5.536 was used for converting ml of $H_2O$ into $c_{H_2O}$
The measurements were carried out at temperatures of 298.00° K.

In FIG. 1, the $E_T$30-values are plotted against ln $c_{H_2O}$.

The straight line is placed through the linear part of the curve. Evaluation is manuel:

$$c^* = \exp[(E_T^° - b)/E_D]$$

$E_T^° = 46.0$ $b = 49.7$ $E_D = 2.07$ $\rightarrow c^* = 0.17$

The exact value—taking into account all the measuring points—is 0.15 (POLAR-computed).

Where evaluation is by computer, results characterised by even better correlation are obtained.

Table III below shows the values obtained by machine evaluation using the POLAR program.

TABLE III

| $c_{H_2O}$ (Mol/l) | $E_T$ 30 | ln $c_{H_2O}$ | ln $(c/c^* + 1)$ |
|---|---|---|---|
| 0.055 | 46.6 | −1.59 | 0.32 |
| 0.111 | 46.9 | −1.35 | 0.56 |
| 0.166 | 47.5 | −1.16 | 0.75 |
| 0.221 | 47.6 | −1.00 | 0.91 |
| 0.277 | 48.3 | −0.86 | 1.05 |
| 0.332 | 48.1 | −0.73 | 1.18 |
| 0.388 | 48.4 | −0.62 | 1.29 |
| 0.443 | 48.7 | −0.53 | 1.38 |
| 0.498 | 48.9 | −0.44 | 1.47 |
| 0.554 | 48.7 | −0.35 | 1.56 |
| 0.830 | 49.6 | −0.02 | 1.89 |
| 1.107 | 50.2 | 0.23 | 2.14 |
| 1.661 | 51.1 | 0.59 | 2.50 |
| 2.214 | 51.6 | 0.86 | 2.77 |
| 2.768 | 52.2 | 1.07 | 2.98 |
| 3.322 | 52.6 | 1.24 | 3.15 |
| 3.875 | 52.8 | 1.39 | 3.30 |
| 4.429 | 53.3 | 1.52 | 3.43 |
| 4.982 | 53.2 | 1.64 | 3.54 |
| 5.536 | 52.7 | 1.74 | 3.65 |
| 8.304 | 54.0 | 2.13 | 4.04 |
| 11.072 | 54.4 | 2.42 | 4.33 |
| 16.608 | 55.3 | 2.82 | 4.73 |
| 22.144 | 55.9 | 3.10 | 5.01 |
| 27.680 | 56.5 | 3.33 | 5.24 |
| 33.216 | 57.2 | 3.51 | 5.42 |
| 38.752 | 57.9 | 3.66 | 5.57 |

Correlation coefficient: 0.99877 Sigma ED: 0.023580
Statistical evaluation of the measured values.

Figure 2:
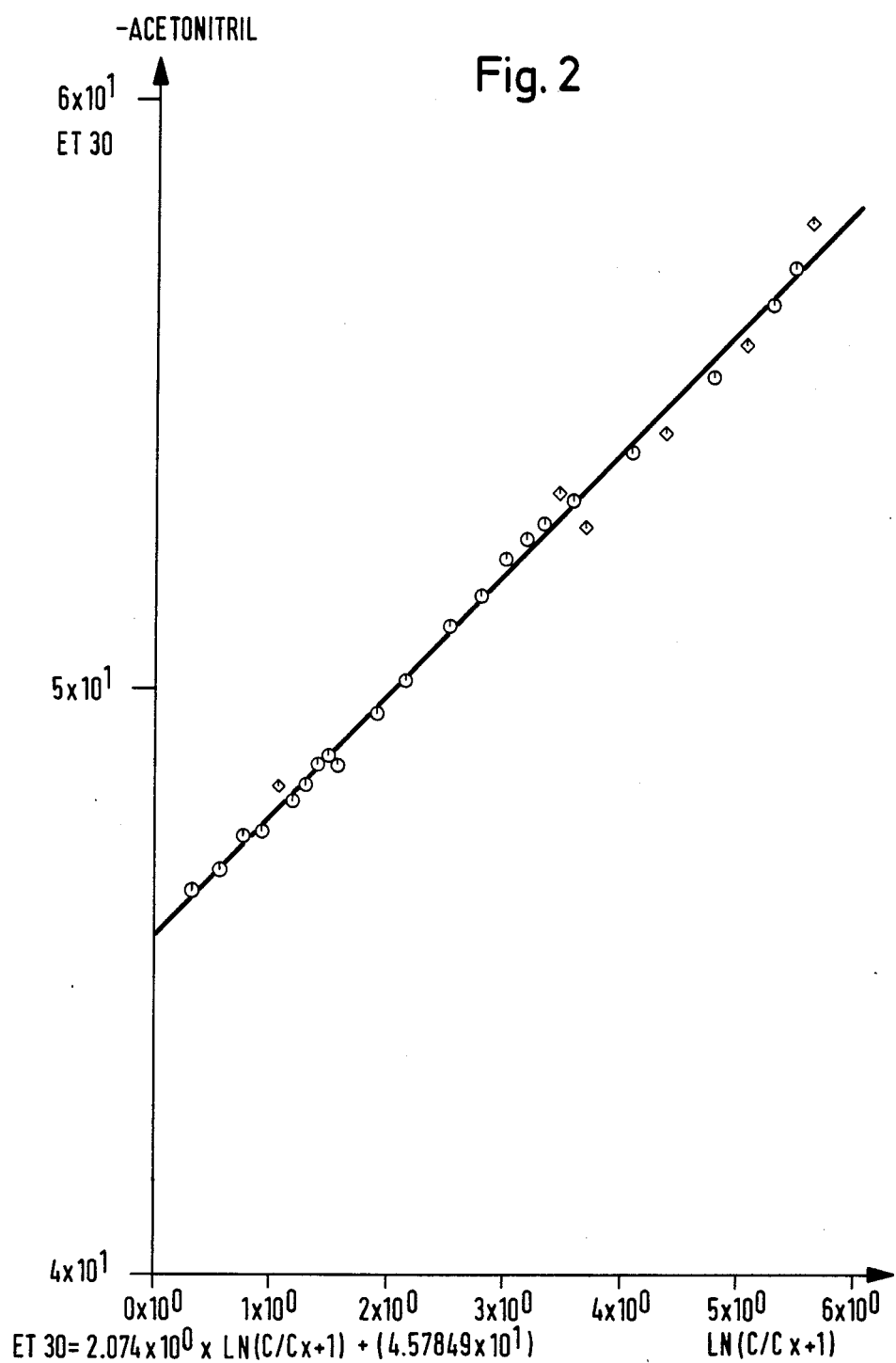

The results of machine evaluation are shown in FIG. 2 Plotting of $$E_T 30 \rightarrow \ln\left(\frac{c_{H_2O}}{c^*} + 1\right)$$

CALCULATION EXAMPLE

Measured wavelength of a solution of unknown water content:

$\lambda_{max} = 541.4 \text{ nm} \rightarrow E_T 30 = 52.8$ (according to equation 2)
Constants according to equation 1 (Tab. 1)

$E_T^° = 46.0; E_T^°/E_D = 22.2$
$E_D = 2.07$
$c^* = 0.15$
$c_{H_2O} = c^* \cdot \exp(E_T/E_D - E_T^°/E_D) - c^*$
$c_{H_2O} = 3.9 \text{ mol} \cdot l^{-1}$
(set value = 3.88 mol · $l^{-1}$)

The error may be reduced even further with better equipment.

What is claimed is:

1. In a process for determining the unknown water content of a liquid organic solvent material, wherein a solvatochromic compound is added and the $\lambda_{max}$ values are determined in the UV/VIS spectrum, and wherein the $E_T$ values are calculated from the $\lambda_{max}$ values, and wherein the $E_T^°$ value of said liquid organic solvent in its anhydrous state is known or determined, the improved process comprising determining standard reference values by preparing several mixtures of said liquid organic solvent with water at different respective water contents, adding the same amount of a solvatochromic compound to each said mixture, then obtaining the $\lambda_{max}$ value for each in the extinction range from 0.4 to 1.2, calculating the $E_T$ value for each said mixture from its $\lambda_{max}$ value, calculating the molar concentration of water in each said mixture, plotting the $E_T$ values from the ordinate against the values from the abcissa of the logarithms of the water concentrations by weight of said mixtures, respcetively, and drawing a stright line through the linear part of said plotted values, determining the slope $E_D$ of said straight line, determining the value "b" of the ordinate section, measured on the ordinate, at the point on said straight line at the zero value of the logarithm of the water concentration $c_{H_2O}$, then:

adding said amount of said solvatochromic compound to, and obtaining the $\lambda_{max}$ for, said material, calculating the $E_T$ value for said material using the observed $\lambda_{max}$, calculating the value of a constant, $c^*$, according to the equation:

$$c^* = e^{[(E_T^° - b)/E_D]}$$

and then calculating the water content of said material in molar percentage according to the equation $$c_{H_2O} = c^{*(E_T/E_D - E_T^°/E_D)} - c^*$$

where $E_T$ in the equation is the $E_T$ calculated for said material from its said $\lambda_{max}$.

2. The process of claim 1 wherein the $\lambda_{max}$ lies in the extinction range of from 0.6 to 1.0.

3. The process of claim 1 wherein the water concentration determination is carried out by a visual color comparison with a color scale.

4. The process of claim 1 wherein the solvatochromic compound is absorbed to a solid material and the water concentration determination is carried out with this solid material.

5. The process of claim 1 wherein the material sample to be analyzed is an organic solvent having a low water content or a water containing gas which is passed through a high-boiling solvent or a solid sample which is dissolved or suspended in a solvent.

6. The process of claim 5 wherein the solvent is acetone, acetonitrile, tert.-butyl alcohol, tert.-butyl hydroperoxide, dimethyl formamide, 1,4-dioxane or pyridine.

7. The process of claim 6 wherein the solvatochromic compound is a pyridinium phenol betaine of the formula

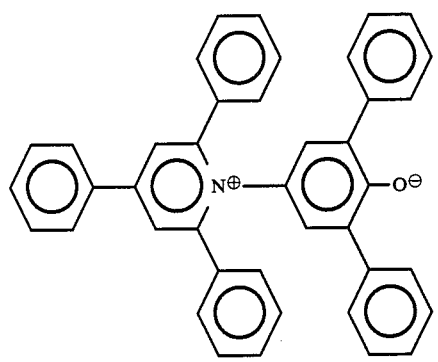

or a Kosower's dye of the formula

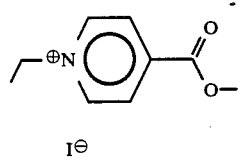

8. The process of claim 7 wherein the determinations are carried out at a constant temperature.

9. The process of claim 1 wherein the $E_T$ value is calculated according to the equation $$E_T = 28,590 \; Kcal \cdot nm \cdot mol^{-1}/\lambda_{max}.$$

10. The process of claim 9 wherein the $\lambda_{max}$ lies in the extinction range of from 0.6 to 1.0.

11. The process of claim 9 wherein the material sample to be analysed is an organic solvent having a low water content or a water containing gas which is passed through a high-boiling solvent or a solid sample which is dissolved or suspended in a solvent.

12. The process of claim 11 wherein the solvent is acetone, acetonitrile, tert.-butyl alcohol, tert.-butyl hydroperoxide, dimethyl formamide, 1,4-dioxane or pyridine.

13. The process of claim 12 wherein the solvatochromic compound is a pyridinium phenol betaine of the formula

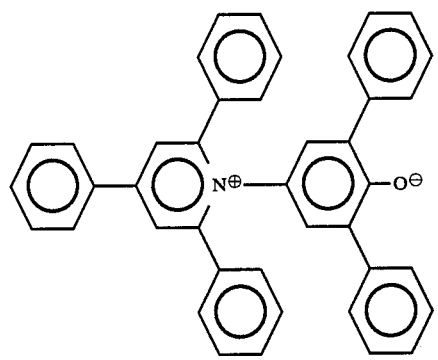

or a Kosower's dye of the formula

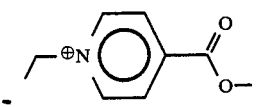

14. The process of claim 13 wherein the determinations are carried out at a constant temperatures in the range from 0° C. to 100° C.

* * * * *